United States Patent [19]
Nowak et al.

[11] Patent Number: 5,817,309
[45] Date of Patent: Oct. 6, 1998

[54] ANTIDOTE FOR HIRUDIN AND SYNTHETIC THROMBIN INHIBITORS AND METHOD OF USE

[75] Inventors: Götz Nowak; Elke Bucha, both of Erfurt, Germany

[73] Assignee: Max-Planck-Gesellschaft, Gottingen, Germany

[21] Appl. No.: 694,831

[22] Filed: Aug. 9, 1996

Related U.S. Application Data

[63] Continuation of Ser. No. 284,458, filed as PCT/EP93/00162 Jan. 25, 1993 published as WO93/15757 Aug. 19, 1993, abandoned.

[30] Foreign Application Priority Data

Feb. 11, 1992 [DE] Germany .......................... 42 03 965.7

[51] Int. Cl.$^6$ ................................................. A61K 38/47
[52] U.S. Cl. ..................... 424/94.61; 424/94.1; 424/542
[58] Field of Search ............................... 424/94.1, 94.61, 424/542

[56] References Cited

U.S. PATENT DOCUMENTS

| | | | |
|---|---|---|---|
| 3,849,252 | 11/1974 | Percs et al. ................................ | 195/62 |
| 4,849,403 | 7/1989 | Stocker et al. .............................. | 514/2 |
| 5,182,260 | 1/1993 | Maraganore et al. ..................... | 514/12 |
| 5,187,102 | 2/1993 | Stocker et al. ............................. | 436/69 |
| 5,196,403 | 3/1993 | Maraganore et al. ..................... | 514/12 |
| 5,242,810 | 9/1993 | Maraganore et al. .................. | 435/69.2 |
| 5,547,850 | 8/1996 | Nowak et al. ............................. | 435/13 |

OTHER PUBLICATIONS

Stocker, Seminars in Thrombon's J. Hemostasis, vol. 17, No. 2, pp. 113–121, 1991.

Teng et al., Biochim. et Biophy. Acta, vol. 841, pp. 8–14, 1985.

Kornalik, F. et al., "Thrombosis and Hemostasis," vol. 50, #1, 1986, p. 267. Abstract #0837.

Merita, T. et al, "Biochem. (Japan)," vol. 79, #5, May 1976. pp. 1089–1108.

Gullin, M.C., et al, "Biochimica et Biophysisc Acta," vol. 537,#1, 1978, pp. 160–168.

Weller, T. et al, "Drugs of the Future," vol. 19, #5, 1994, pp. 461–476.

Moo–Jhong Rhee et al,; Biochemistry 1982, 21, 3437–3443.

Hélène Hofmann, Cassian Bon; Biochemistry 1987, 26, 772–780.

Chemical Abstracts 90 (1979): 82920v; M.C. Guillin et al.; Biochim. Biophys. acta, 1978, 537 (1), 160–168.

Medline: 86225810; R.C. Schaeffer Jr. et al.; Lab. Clin. Med. 1986, 107 (6), 488–497.

*Primary Examiner*—Chhaya D. Sayala
*Attorney, Agent, or Firm*—Sughrue, Mion, Zinn, Macpeak & Seas, PLLC

[57] ABSTRACT

The invention relates to an antidote for hirudin and synthetic thrombin inhibitors; the antidote contains a compound that splits prothrombin into meizothrombin, a prothrombin intermediate, a pharmacologically acceptable salt thereof or a mixture of these compounds, together with conventional vehicles and/or diluents. The present invention also relates to the application of a compound that splits prothrombin into meizothrombin, a prothrombin intermediate, or a pharmacologically acceptable salt thereof or a mixture of these compounds, together with conventional vehicles and/or diluents as an antidote for hirudin and synthetic thrombin inhibitors or for the preparation of an antidote for hirudin and synthetic thrombin inhibitors.

12 Claims, 5 Drawing Sheets

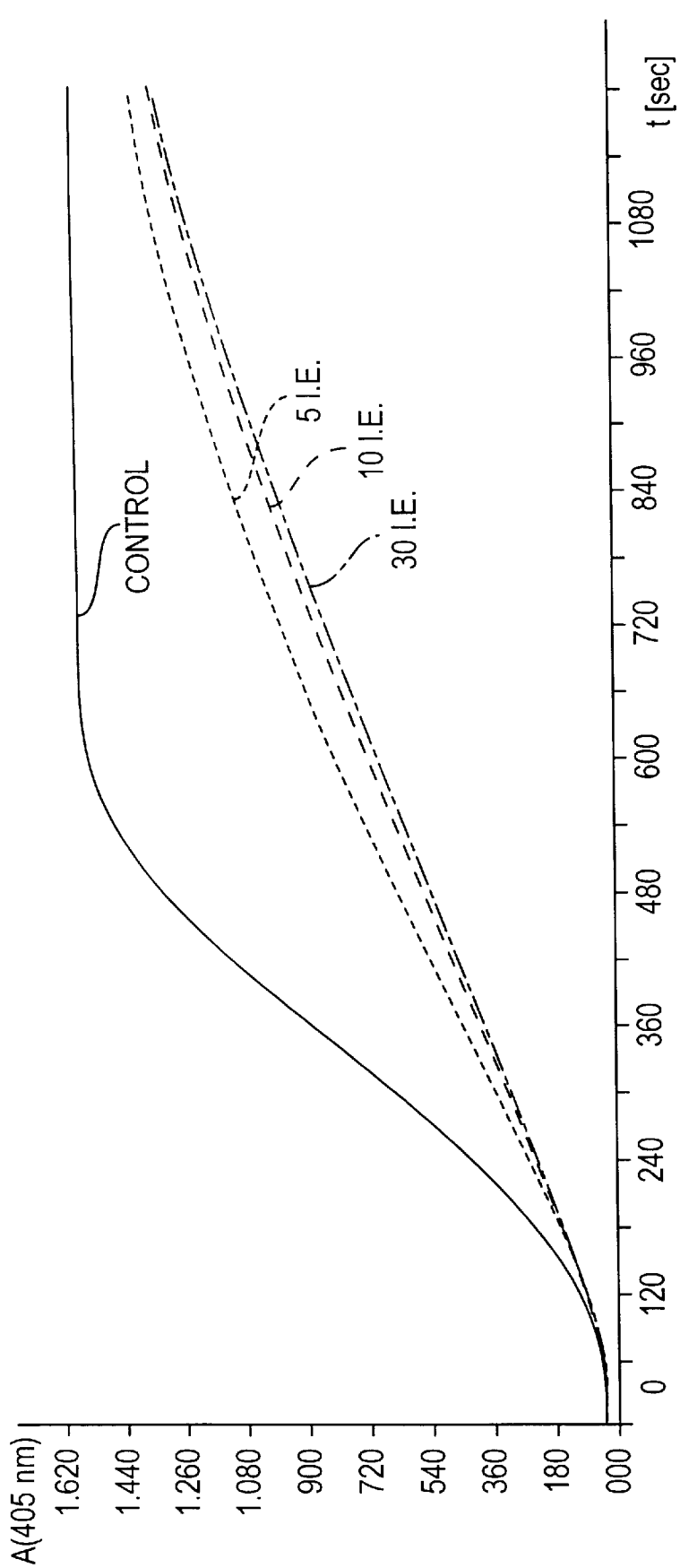

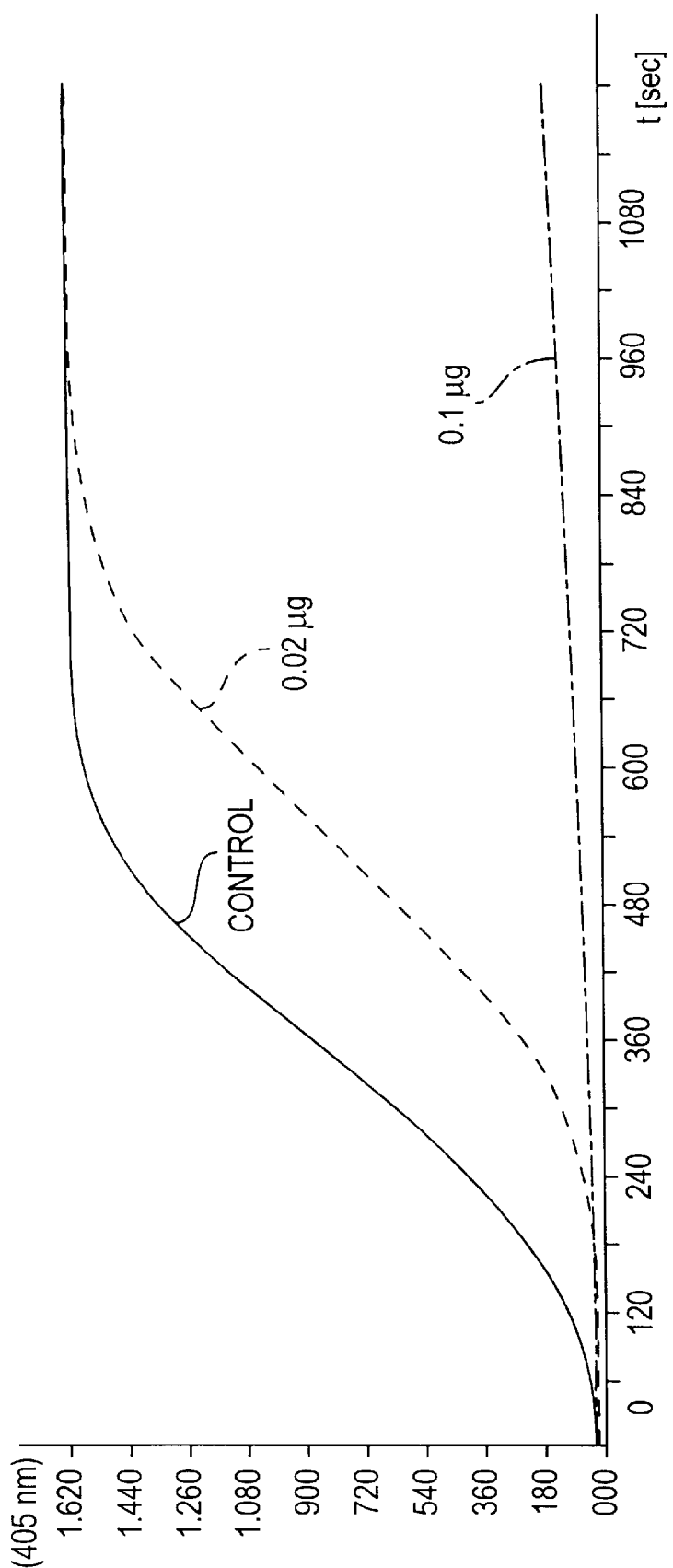

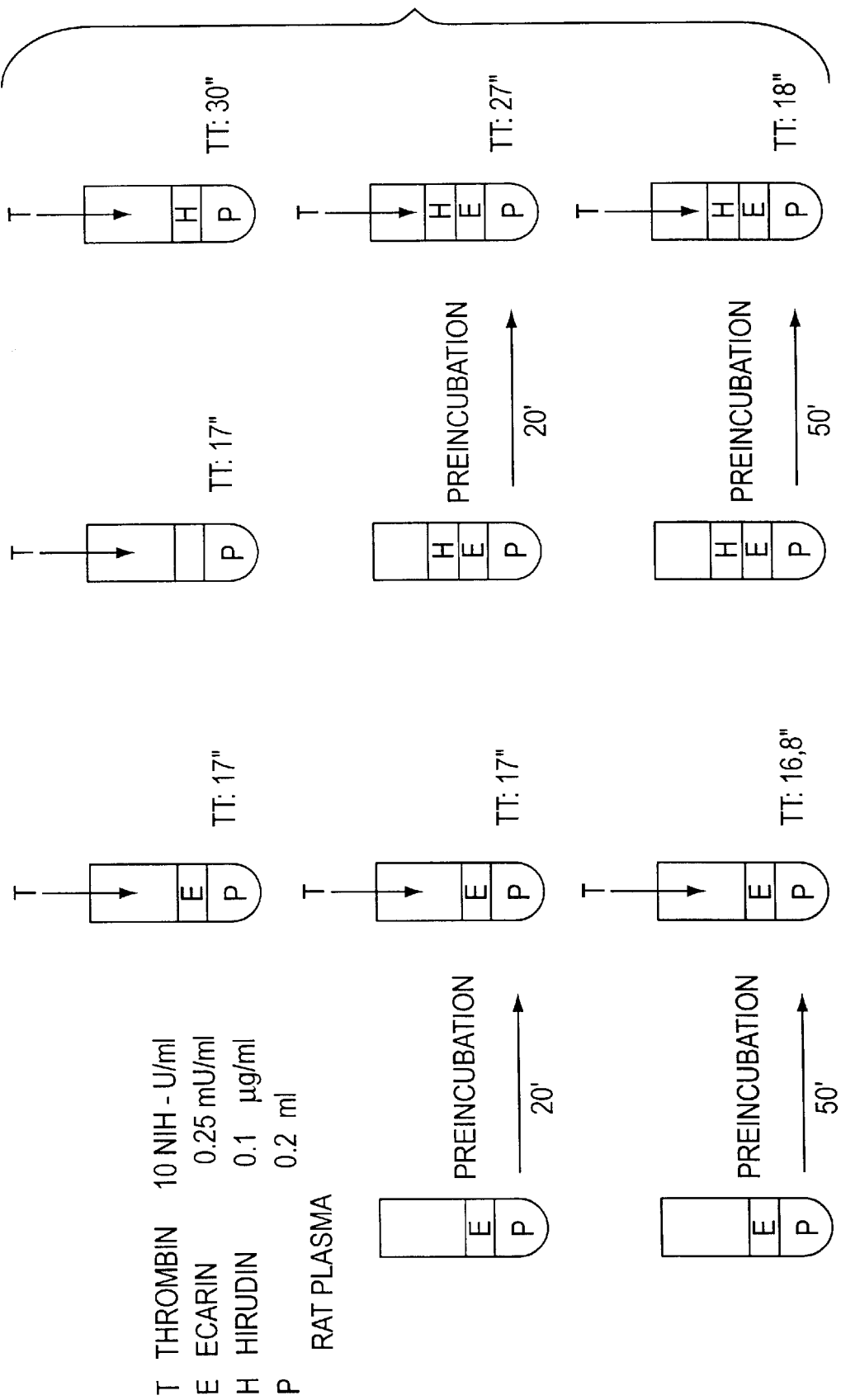

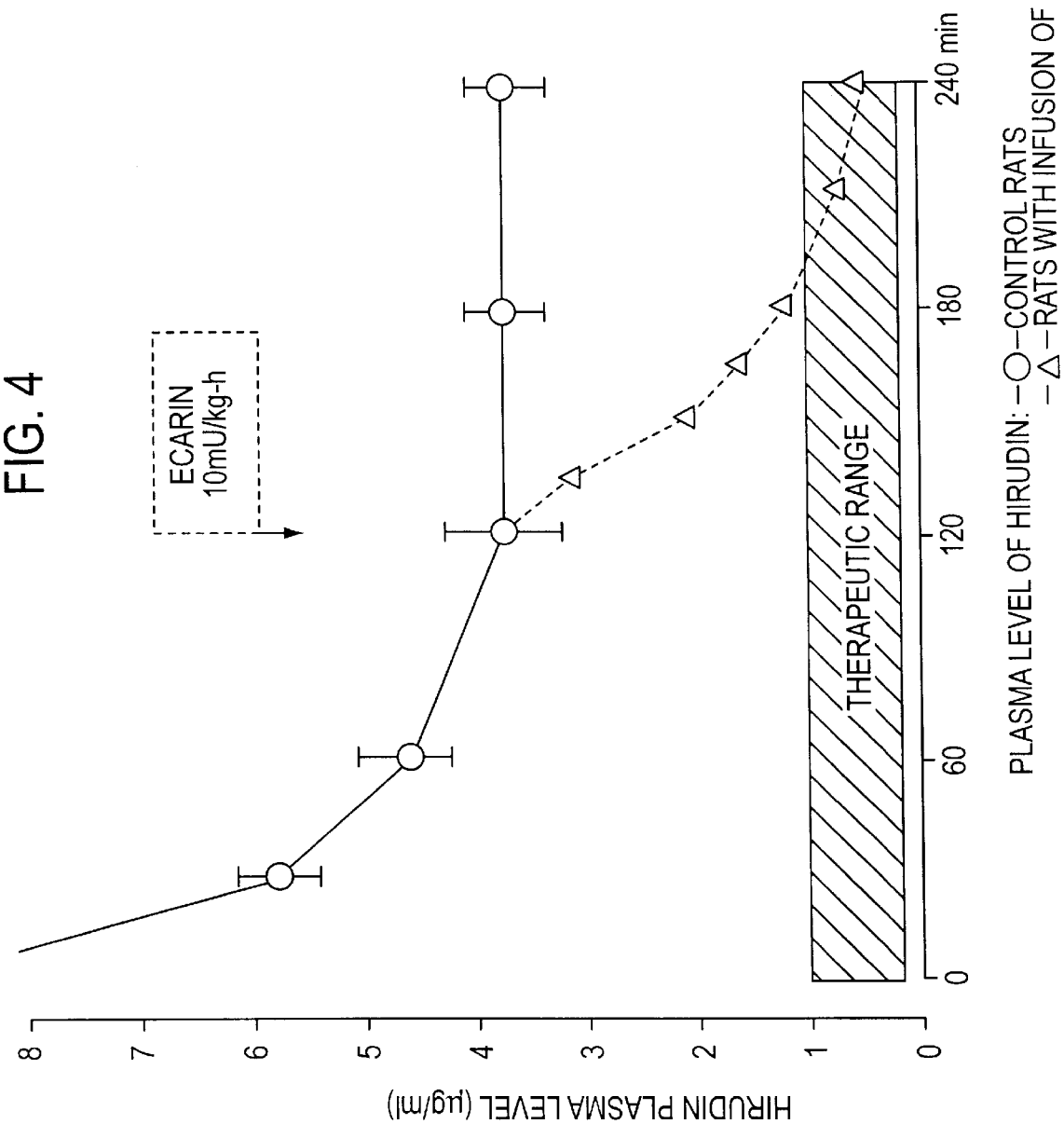

ANTIDOTE FOR HIRUDIN AND SYNTHETIC THROMBIN INHIBITORS AND METHOD OF USE

This is a Continuation of application Ser. No. 08/284,458 filed Dec. 8, 1994, now abandoned, which is the National stage filing of PCT/EP93/00162, filed Jan. 25, 1993.

BACKGROUND OF THE INVENTION

The invention relates to an antidote for hirudin and synthetic thrombin inhibitors, the application of a compound that splits prothrombin into meizothrombin, a prothrombin intermediate or a pharmacologically acceptable salt thereof as the antidote for hirudin and synthetic thrombin inhibitors or for the preparation of an antidote for hirudin and synthetic thrombin inhibitors.

Anticoagulants, such as heparin or coumarins, are often used today for therapy and prophylaxis of thromboembolic diseases, in particular for the treatment of coronary infarctions, arteriosclerosis, furthermore during blood transfusions and following operations. They can also be used as agents to prevent death from exposure, since they prevent the blood from coagulating at extremely cold temperature; otherwise the blood vessels would partially clog and the frozen organs would be cut off from the blood circulation.

Hirudin, which is obtained from the salivary gland of the Hirudo medicinalis (leech), is an anticoagulant, whose effect is based on the formation of a chemical compound with thrombin, whereby its catalytic action is inhibited. Hirudin is a miniprotein comprising 65 amino acids with a molecular weight of 7 kD. Owing to its strong affinity for thrombin ($k_i$ values of $10^{-12}$ mol/l) and its direct mechanism of action, it is of great interest. Its clinical application was extremely limited in the past, since hirudin was not easily accessible in the standardized form and no antidote was available. Today hirudin can be produced through genetic engineering; and, therefore, its clinical application can be expected in the near future.

For example, pharmaceutical preparations for oral administration are described in the EP-A-0 468 327; said preparations contain recombinant hirudin.

Recently hirudin has been intensively investigated pharmacologically; and the pharmacological data were acquired from experimental animals and humans. Hirudin is not metabolized in the liver, but rather eliminated in an unchanged form through the kidneys. Hirudin has an elimination half-life of about 1 to 2 hours and is distributed into the extracellular fluid spaces of the body. Analogous to heparin, hirudin is not resorbed orally. Past investigations have demonstrated that hirudin is active in almost all models of thrombosis, thus even during endotoxic shock and during experimental cardiac infarction and during prevention of reocclusion following thrombolysis. No immunological reactions were detected in the clinical-pharmacological investigations. During clinical investigations hirudin has proven to be superior to heparin as an anticoagulant and antithrombotic agent.

Recently synthetic thrombin inhibitors have gained in importance. Currently many research laboratories are working world-wide on synthesizing such synthetic inhibitors. Investigations with derivatives of benzamidines, such as the small molecular synthetic thrombin inhibitor NAPAP (Nα-(2-naphthylsulforyl-glycyl)-D,L-amidinophenylalanine-piperidide) and with so called tripeptides have made the most progress. All synthetic thrombin inhibitors are currently in preclinical research. Their effects can be equated qualitatively with those of hirudin. However, the metabolism of the synthetic thrombin inhibitors differs from that of hirudin. Usually the thrombin inhibitors are metabolized in the liver or in the blood. It is anticipated that such substances will be available soon for clinical testing. The advantage over hirudin lies predominantly in the fact that the compounds can be administered orally.

Despite the beneficial effects, hirudin has not been used to date clinically or its use has been quite limited, since, as aforementioned there is no antidote, as, for example, in the case of heparin there is protamine sulfate. The presence of an antidote is absolutely necessary for a thrombin inhibitor, because in the case of accidental overdosing or for patients with kidney function disorders, for whom there is the risk of bleeding complications, an antidote must be on hand immediately, should overdosing be determined. Such bleeding complications occur, for example, as hemorrhagic side effects, above all in the vascular regions of the peritoneum, the pleura, the pericardium and the pia mater, but also in wounds from surgical incision, as observed in animals with extremely high blood levels of a thrombin inhibitor.

In the past different antidote principles for hirudin have been experimentally researched; thus the use of gamma thrombin preparations, like DFP thrombin or benzoyl thrombin (Brüggener, E., Walsmann, P., Markwardt, F. "Neutralization of Hirudin Anticoagulant Action by DIP-Thrombin." Pharmazie 1989; 44: 648–9). These preparations have not been successful in practice and they are too toxic. Even activated plasma fractions, like FEIBA or autoplex preparations, are unsuitable owing to the thromboplastin-similar activity (Fareed, J., Walenga, J.M., "Do we need to neutralize hirudin's anticoagulant effects to minimize bleeding?" Fed Proc 1989; 3: A328; Walenga, J. M, Piffarre, R., Hoppensteadt, D. A., Fareed: "Development of recombinant hirudin as a therapeutic anticoagulant and antithrombotic agent. Some objective considerations." Sem Thromb Hemost 1989; 15: 316–33).

SUMMARY OF THE INVENTION

The present invention is based on the problem of providing an antidote for hirudin and synthetic thrombin inhibitors. The antidote shall be quite effective, i.e. exhibit an adequate affinity for hirudin and synthetic thrombin inhibitors; its dosing shall be simple and it shall be readily accessible.

The subject matter of the invention is an antidote for hirudin and synthetic thrombin inhibitors, which is characterized in that it contains a compound that splits prothrombin into meizothrombin, a prothrombin intermediate, a pharmacologically acceptable salt thereof or a mixture of these compounds, together with conventional vehicles and/or diluents, whereby it contains as the prothrombin intermediate meizothrombin, PIVKA prothrombin, meizothrombin-des-fragment-1 or a compound containing meizothrombin.

The subject matter of the invention is also the application of a compound that splits the prothrombin into meizothrombin, a prothrombin intermediate defined above, a pharmacologically acceptable salt thereof or a mixture of these compounds together with the conventional vehicles and/or diluents as the antidote for hirudin and synthetic thrombin inhibitors or for the preparation of an antidote for hirudin and synthetic thrombin inhibitors.

Suitable thrombin inhibitors are, according to the invention, hirudin and synthetic, preferably small molecular, thrombin inhibitors. Examples of synthetic thrombin inhibitors are NAPAP (Nα-(2-naphthylsulforyl-glycyl)-D,L-amidinophenylalanine-piperidide); moreover, the derivatives of tripeptide phe-pro-arg, like boric acid derivatives, argininals, chloromethylketone derivatives and amino acid-modified derivatives and benzamidine derivatives and also socalled hirologs, i.e. synthetic hirudin-analogous partial sequences. For all of these compounds the antidote principle is the same as for hirudin.

DESCRIPTION OF THE DRAWINGS

FIGS. 2A and 2B depict the spectrophotometric measurement of the splitting of a thrombin-specific chromogenic substrate in human plasma with simultaneous presence of heparin (5–30 IU/ml) or of hirudin (0.1–0.2 µg/ml), caused by Ecarin. These figures show that the Ecarin-induced thrombin-like enzyme activity totally splits the chromogenic substrate within about 10 minutes. If heparin has been added to the reaction mix, the substrate splitting will be slightly reduced irrespective of the dose (up to 30 IU/ml heparin). However, hirudin already inhibits in minor concentrations the Ecarin-induced substrate splitting depending on the dose (0.1 µ/ml hirudin fully prevents the formation of enzyme activity). These results show that the heparin-antithrombin III complex cannot block the prothrombin splitting induced by Ecarin in the plasma into meizothrombin. However, if hirudin is added, minor amounts of this thrombin inhibitor can inhibit the amidolytic activity of the Ecarin-induced meizothrombin formation.

FIG. 3 illustrates test results obtained to the effect that the hirudin-caused prolongation of the thrombin period can be cancelled when the hirudin-containing human plasma is preincubated with Ecarin. If a minor amount of Ecarin is added to human plasma, the thrombin period for this reaction mixture will be unchanged as compared to the Ecarin-free control (17 sec., upper row). If the human plasma is admixed with hirudin (0.1 µg/ml), the thrombin period is prolonged to 30 sec. The pre-incubation of such hirudin-containing plasma with Ecarin reduces the thrombin period as a function of time, one minute already being sufficient to consume almost the entire hirudin existing in the reaction mixture by the meizothrombin formed.

FIG. 4 depicts the influence of Ecarin on the hirudin blood level of nephrectomized rats. After the application of 1 mg/kg of hirudin in nephrectomized rats, a constant blood level of hirudin is reached after about 2 hours. When Ecarin is infused into these animals over a prolonged period of time beginning 120 minutes after hirudin-bolus, the blood level of hirudin will drop relatively rapidly. Ecarin, which is constantly available in the blood circulation, splits prothrombin into meizothrombin. This inhibits the hirudin present in the blood. It is also of interest that, upon completion of the Ecarin infusion, the blood level continues to drop, so that in the further course the toxic hirudin level reaches again the standard range of a therapeutically acceptable dosage.

DETAILED DESCRIPTION OF THE INVENTION

Figure 1:
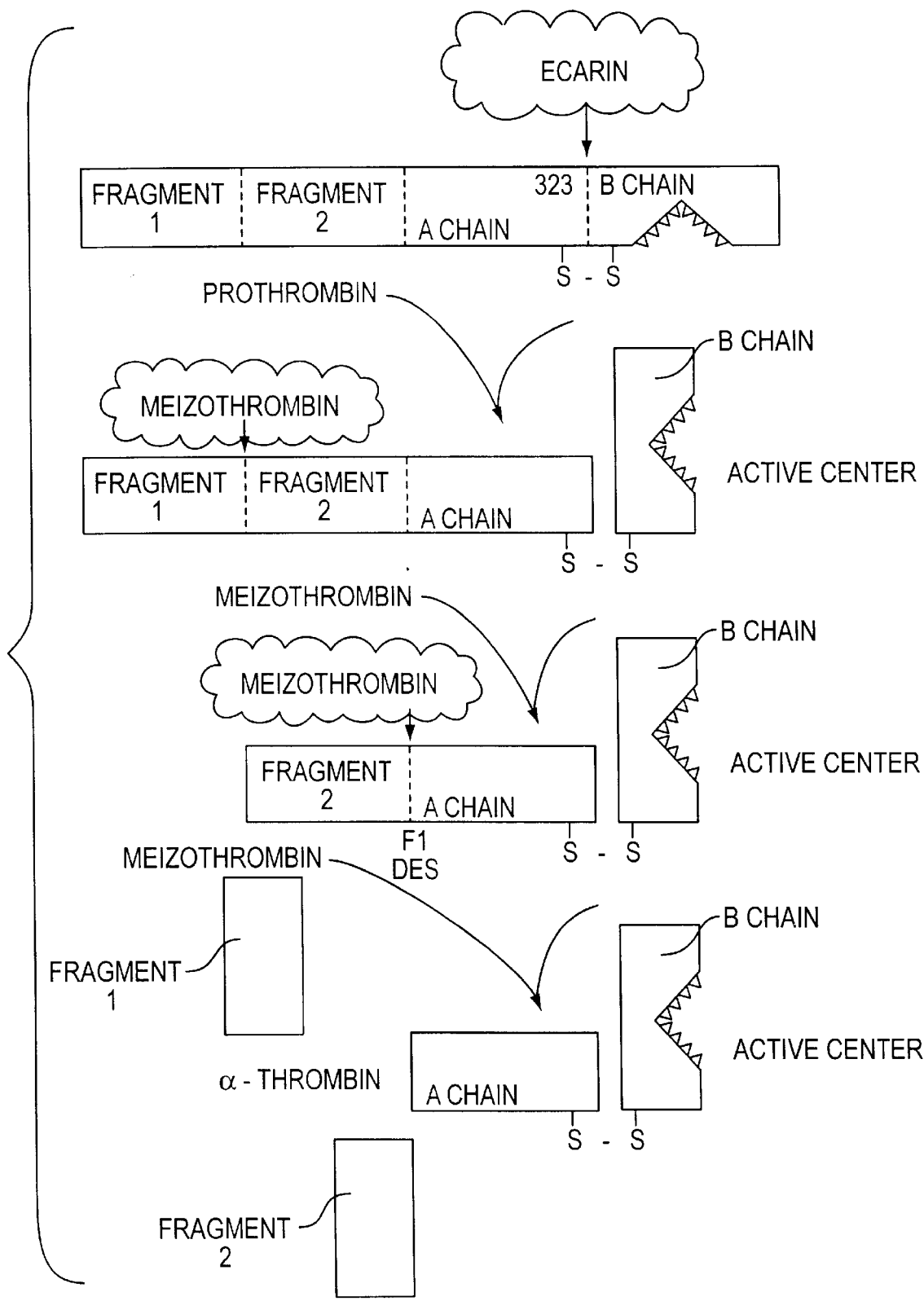
FIG. 1 is a schematic depicting Ecarin-induced activation. In the A chain of prothrombin, Ecarin splits the peptide bond at $Arg^{323}$. As a result, the active center of thrombin is partially exposed even though the entire A chain is still linked with the B chain via a disulfide bridge (prothrombin and meizothrombin have the same molecular weight). The A chain portions impede the free availability of the active center, above all for large molecules, for linking to the active center molecules such as the antithrombin III-heparin complex, but they do not impede the linkage of low-molecular compounds, e.g., synthetic thrombin inhibitors, thrombin-specific chromogenic substrate or hirudin. Meizothrombin-des-F1 and then alpha-thrombin form only in further proteolytic steps by the effect of thrombin traces and, under certain circumstances, also via autocatalytic processes.

The antidote according to the invention exists in a suitable form for parenteral administration, i.e. a form that is suitable for the subcutaneous, intramuscular or intravenous administration. Intravenous administration is preferred. Optionally the antidote according to the invention can also be administered as continuous infusion.

According to the invention, snake venom is used as the compound that splits prothrombin into meizothrombin. Examples of snake venom are Ecarin and poisons from Dispholidus, Rhabdophis, Bothrops, Notechis, Oxyuranus and Russel viper types. Preferred is Ecarin, a purified poison fraction from Echis carinatus toxin. All of the snake venoms can be acquired as biochemicals, for example, at Sigma Chemie GmbH, 8024 Deisenhofen. Purified fractions of individual, listed snake venoms can be acquired upon inquiry at Pentapharm company in Switzerland. The snake venoms, especially Ecarin and immobilized Ecarin, can also be purchased from the Pentapharm company in Switzerland.

The poisons are available as a dry substance, usually freeze-dried, in amounts ranging from 5 mg to 1 g. All poisons are readily water soluble and should be absorbed with 0.9% saline solution. The amount of the dose can be easily determined by the expert. The dose is a function of the body weight, the hirudin content and the method of administration. The amounts used range for one person weighing 70 kg from 0.5 to 5 mg.

According to the invention, meizothrombin, meizothrombin-des-fragment-1, or PIVKA prothrombin or a compound containing meizothrombin is used as the prothrombin intermediate. Meizothrombin is commercially available and can also be obtained from the aforementioned Pentapharm company. However, meizothrombin, PIVKA-prothrombin, meizothrombin-des-fragment-1, or other prothrombin intermediates can also be formed in vitro.

As shown in the following diagram, four factors of the coagulation system—factor II (prothrombin), factor VII, factor IX and factor X—are characterized in that they contain gamma-carboxyglutamic acid groups. This gamma-carboxylation at the glutamic acid does not take place until after the ribosomal synthesis of the "acarboxy factor" in the liver with the aid of an enzyme system, which requires vitamin K as the cofactor.

Therapeutic Mechanism of Vitamin K and Coumarins

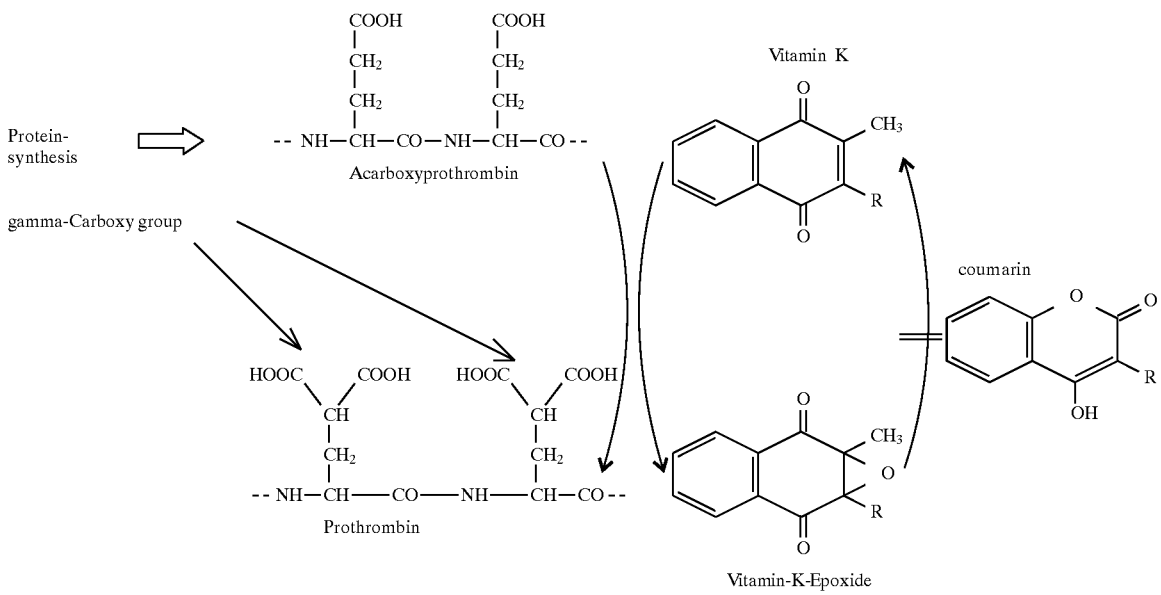

The gamma-carboxyglutamic acid groups are essential for the coagulation action. They represent the necessary bonding valences for calcium ions. For treatment with indirect anticoagulants of the Dicumarol type ("vitamin K antagonists"), the postribosomal gamma-carboxylation cannot take place; and the blood exhibits incomplete coagulation factors or acarboxy factors, because they lack the calcium-binding gamma-carboxy groups. These coagulation factors are also called PIVKA factors (PIVKA=proteins induced by vitamin K antagonists).

When Ecarin is added to the plasma of patients treated with such anticoagulants of the Dicumarol type, PIVKA meizothrombin is produced in this plasma from the PIVKA prothrombin in the same manner through a limited proteolysis, as is also the case in normal plasma samples with prothrombin.

This PIVKA meizothrombin or other PIVKA intermediates have retained their ability to bond with hirudin, but they have no or significantly less effect on other factors of the coagulation cascade (platelets, fibrinogen, thrombomodulin etc.). According to the invention, meizothrombin, PIVKA meizothrombin, their intermediates and PIVKA intermediates from PIVKA prothrombin can be used as the antidote. They can originate from humans or from other mammals.

To prepare meizothrombin immobilized Ecarin (product of Pentapharm AG, Basel) can be packed, for example, in mini columns ranging in size from 2–4 cm$^3$ for example. Ecarin immobolizate is afforded in the swollen state, suspended in an aqueous solution of sodium chloride 0.15 M, sodium acetate 0.02 M, Prionex (R) (trademark of Pentapharm AG from a protein-stabilizing polypeptide fraction from cleaned pig skin collagen) 0.2% and trichloroisobutanol 0.3%, pH 5.5. One gram of swollen Ecarin immobilizate produces from barium citrate eluate at 37° C., pH 8.4, within 30 minutes 500 to 700 U amidolytic activity (1 U=123 NIH units), measured at tos-gly-pro-arg-pNA (Chromozym (R) TH).

Then purified prothrombin fractions are put on these columns; and the formed meizothrombin, optionally following stabilization with heparin, is subsequently freeze-dried. The freeze-dried material can be packed into ampoules and then reconstituted with a suitable solvent, preferably with sterilized sodium chloride solution, which is suitable for intravenous injection, for application as an antidote.

To prepare meizothrombin-des-fragment-1, the same process as for meizothrombin is used. In the batch process only a longer reaction time (3–4 hours) has to be planned. Meizothrombin-desfragment-1 is a product following the activation of meizothrombin.

For parenteral administration the antidote can be formulated for the injection, like the intravascular, e.g. intravenous, intramuscular or subcutaneous, injection. The intravascular administration is preferred. Preparations for the injection can be on hand as one dose, for example in ampoules, or in multiple dose containers with added preservative. The preparations can exist as suspensions, solutions or emulsions in oily or aqueous carriers, and contain preparation aids, such as suspending, stabilizing and/or dispersing agents, and/or agents for adjusting the tonicity of the solution. As an alternative the active ingredient can be present as a powder for constituting with a suitable carrier, for example sterilized pyrogen-free water, prior to application.

In ampoules and multiple dose containers for intravascular application, the product, e.g. the meizothrombin, should exist preferably in the freeze-dried state. In this form it is completely soluble in sterilized water, physiological saline solution or buffer solutions, which contain $Ca^{++}$ ions and are adjusted to a pH value ranging from 6.5 to 7. The ampoules should contain 0.5; 1; 2 or 5 mg of meizothrombin; multiple dose containers should contain 10; 20 or 50 mg. A short-term storage (days–1 month) is also possible in the deep-frozen state (−25° C.). For extravascular parenteral application mixtures with 1% Dimeticon suspensions, 5% erythrocyte membrane fragments or barium sulfate emulsions are suitable. Even a liposome adsorption for extravascular application is suitable. The content of the single formulation of meizothrombin is equivalent in these preparations to the filling into ampoules and multiple doses as for intravascular application.

According to the invention, preferably Ecarin, a highly purified fraction of Echis carinatus toxin, is used as the snake venom. Ecarin splits a peptide bond at arginine 323 of the prothrombin, producing the intermediate meizothrombin. Normally the additional reaction occurs through autocatalysis or through thrombin acceleration. When hirudin or synthetic thrombin inhibitors are present in the blood, the meizothrombin and the inhibitor interact. In contrast, heparin cannot react with meizothrombin. The attached FIG. 1 shows these actions.

It could be demonstrated that in highly diluted human plasma due to Ecarin the prothrombin activation is induced. The thrombin/meizothrombin activity was measured with Chromozym (R) TH. FIG. 2 shows the results that were obtained. The dose independent residual activity that could be detected with amounts of heparin ranging from 2.5–35 IE/ml corresponds to the degree to which meizothrombin is formed following the effect of Ecarin. As a function of the dose, hirudin totally inhibits the formation of meizothrombin/thrombin.

To confirm the effect of the antidote, various pharmacological tests were conducted. The antidote effect of the antidote according to the invention was proven in rat tests. FIG. 3 shows the results that were obtained. Rat citrate plasma was made to coagulate with thrombin. The controls have coagulation times of 17 seconds on average. If 0.1 μg hirudin/ml are added to the test batch, the thrombin time is extended to 30 seconds. If the batch with 0.25 mU of Ecarin/ml is preincubated, the thrombin time drops to 27.5 seconds, following a preincubation period of 20 seconds, owing to the consumption of hirudin in the plasma. At a 50 second preincubation the thrombin time matches the control value (without addition of hirudin). The Ecarin concentration itself that was used does not cause the coagulation to accelerate in the test batch in this time range.

To confirm the antidote action, constant blood levels of hirudin in the range of 3.5 to 4.2 μg/ml following intravenous application of 1 mg/kg hirudin were also produced in nephrectomized rats. During the infusion of 50 μg of Ecarin/kg $h^{-1}$, the hirudin level drops rapidly and is significantly reduced to 2.1 μg/ml just after 30 minutes following the start of application. At the end of the toxin infusion the blood level has decreased to 1.2 μg/ml. Rebound phenomena are not observed. The finding that in these tests the platelet count and the fibrinogen level remained virtually unchanged has to be evaluated as especially important. Even when the Ecarin infusion duration was reduced to 30 or 15 minutes, and thus the dose was reduced by half or to a fourth, this drop in the hirudin level can also be proven in a similar manner (cf. FIG. 4).

In another series of tests, the antidote mechanism was confirmed with a bleeding model. To this end, nephrectomized rats were administered intravenously 5 mg/kg of hirudin. After 2 hours a constant blood level of 18 μg/ml of hirudin was reached. At this instant a bleeding time of longer than 100 minutes was measured. If the rats are infused with Echis-carinatus toxin (1 mg/kg $h^{-1}$), then the bleeding ceases after 90 minutes. The blood loss from the experimental incised cut is significantly reduced; the hirudin blood level has fallen to values ranging from 1 to 3 μg/ml. The following table shows the results that were obtained.

Ecarin-Induced Meizothrombin Formation as Antagonism Against Toxic Hirudin Blood Levels in Rats;

Ecarin-Induced Meizothrombin Formation as Antagonism Against Toxic Hirudin Blood Levels in Rats

| time (h) | test log | plasma level of hirudin (μg/ml) | bleeding time* (min.) | blood loss |
|---|---|---|---|---|
| 0 | bilateral nephrectomy | | | |
| 2 | | 0 | 2.52 | – |
| 2 | hirudin i.v. (5 mg/kg) | | | |
| 4 | | 17.8 | >30 | +++ |
| 4 | E. carinatus toxin infusion (1 mg/kg · $h^{-1}$) prothrombin substitution | | | |
| 5 | | 5.9 | 8.17 | (+) |
| 6 | | 3.5 | 6.40 | – |

(* incision into the abdominal wall)
"–" means no bleeding
"(+)" means minor bleeding
"+++" means intensive bleeding It is clear from the above tests that Ecarin, acts as an indirect antidote against hirudin intoxications. The Ecarin transforms prothrombin in the plasma to meizothrombin, which is the direct antidote. Similar pharmacological results were obtained with other prothrombin intermediates.

The following examples explain the invention.

EXAMPLE 1

Preparation Of Meizothrombin In Batch Process 500 ml Of Prothrombin Solution:

Prothrombin is precipitated by means of $BaSO_4$ from 2 liters of oxalate plasma and subsequently washed with 0.1 M of sodium oxalate and 0.006 M of sodium citrate at pH 7.5. Following elution of the prothrombin with 0.15 M of sodium citrate and pH adjustment to 7.5, an alcohol precipitation (19%) is conducted at −5° C. The supernatant is adjusted to pH 5.5. and the alcohol concentration is increased to 25%. The precipitate is dissolved and heated to 50° C. for 5 minutes, centrifuged at 6000 g and then filled to 500 ml with acetate buffer.

50 mg of human prothrombin dissolved in 500 ml of acetate buffer at pH 5.5 are stirred with 10 g of immobilized Ecarin for 60 minutes at 20° C. Following centrifugation (15 minutes at 6000 g) the supernatant is calibrated with the aid of a calibration curve, which was obtained with a meizothrombin standard, to 1 mg/ml, filled into 10 ml ampoules, freeze-dried and heat-sealed. The filling was conducted with simultaneous sterilization under aseptic conditions. Following freeze-drying, the ampoules are sealed and stored at 4° C. In this form the preparations can be stored for at least 12 months without any activity loss.

EXAMPLE 2

Preparation Of PIVKA Meizothrombin In The Column Process 250 ml of acetic acid buffer solution (pH 5.5.), containing 25 mg of PIVKA prothrombin (preparation according to example 1, starting material 1 liter of oxalate plasma, obtained by pooling the plasma of patients treated with Dicumarol) are eluted over 40 $cm^3$ columns (50–75 cm length), packed with 10 g of swollen Ecarin immobilizate. The eluted volume is limited to 500 ml, subsequently sterilized by filtration (with sterilized filters) and then filled into ampoules in 10 ml portions. Following freeze-drying, the ampoules are sealed and stored in the same manner as described in example 1.

EXAMPLE 3

The lyophilized 1 mg ampoules are dissolved with 10 ml of 0.9% NaCl and administered in this form. For intravenous infusion multiple dose containers, containing 10 mg of meizothrombin, are dissolved with 0.9% NaCl and administered in 500 ml of 0.9% Nacl infusion solution each. The rate of infusion should be about 1000 ml/h. The plasma hirudin content must be controlled continuously with a bedside method.

Variations of the invention will be apparent to the skilled artisan.

We claim:

1. A parenterally administrable antidotal composition for hirudin and for synthetic thrombin inhibitors, said composition containing (A) a hirudin or a synthetic thrombin inhibitor antidotal amount of a component selected from the group consisting of (1) a snake venom or a purified fraction thereof or a pharmacologically acceptable salt of said venom or fraction that splits prothrombin into meizothrombin, (2) a prothrombin intermediate or a pharmacologically acceptable salt of said prothrombin intermediate, said intermediate selected from the group consisting of meizothrombin, PIVKA prothrombin, meizothrombin-des-fragment-1 and a compound containing meizothrombin and (3) a mixture of (1) and (2), and (B) a conventional parenterally administrable vehicle.

2. The parenterally administrable antidotal composition according to claim 1, wherein the composition is suitable for subcutaneous, intramuscular or intravascular administration.

3. The parenterally administrable antidotal composition of claim 1, wherein the purified fraction of snake venom is ecarin.

4. The antidotal composition according to claim 1, said composition containing a snake venom or a purified fraction thereof or a pharmacologically acceptable salt of said venom or fraction that splits prothrombin into meizothrombin.

5. The antidotal composition according to claim 4, said composition containing said purified fraction wherein said purified fraction is ecarin.

6. The antidotal composition according to claim 1, said composition containing a prothrombin intermediate or a pharmacologically acceptable salt of said prothrombin intermediate, said intermediate selected from the group consisting of meizothrombin, PIVKA prothrombin, meizothrombin-des-fragment-1 and a compound containing meizothrombin.

7. A process for administering to a patient in need thereof an antidote for hirudin or for a synthetic thrombin inhibitor which comprises parenterally administering to the patient an antidotal effective amount of the composition of claim 1.

8. The process of claim 7, wherein the snake venom is ecarin.

9. The process of claim 7, wherein the antidotal composition is administered subcutaneously, intramuscularly or intravascularly.

10. The process according to claim 7, wherein said composition contains said snake venom or said purified fraction thereof or said pharmacologically acceptable salt of said snake venom or fraction.

11. The process according to claim 10, wherein said snake venom is ecarin.

12. The process according to claim 7, wherein said composition contains said prothrombin intermediate or said pharmacologically acceptable salt of said prothrombin intermediate.

* * * * *